United States Patent
Han et al.

(10) Patent No.: US 9,239,391 B2
(45) Date of Patent: Jan. 19, 2016

(54) APPARATUS AND METHOD FOR DISTINGUISHING ENERGY BANDS OF PHOTONS IN MULTI-ENERGY RADIATION

(75) Inventors: Sang-wook Han, Busan (KR); Hyun-sik Kim, Daejeon (KR); Jun-hyeok Yang, Daejeon (KR); Gyu-hyeong Cho, Daejeon (KR); Young-hun Sung, Hwaseong-si (KR)

(73) Assignees: Samsung Electronics Co., Ltd., Suwon-si (KR); Korea Advanced Institute of Science and Technology, Daejeon (KR)

( * ) Notice: Subject to any disclaimer, the term of this patent is extended or adjusted under 35 U.S.C. 154(b) by 679 days.

(21) Appl. No.: 13/561,503

(22) Filed: Jul. 30, 2012

(65) Prior Publication Data

US 2013/0041628 A1 Feb. 14, 2013

Related U.S. Application Data

(60) Provisional application No. 61/522,782, filed on Aug. 12, 2011.

(30) Foreign Application Priority Data

Oct. 5, 2011 (KR) .................. 10-2011-0101410

(51) Int. Cl.
*G06F 15/00* (2006.01)
*G01T 1/17* (2006.01)
(Continued)

(52) U.S. Cl.
CPC . *G01T 1/17* (2013.01); *A61B 6/032* (2013.01); *A61B 6/4241* (2013.01); *G01T 1/16* (2013.01); *G01T 1/2928* (2013.01)

(58) Field of Classification Search
CPC ....... G01T 1/2928; G01T 1/17; G01T 1/2018; G01T 1/242; G01T 1/243; G01T 1/249; G01T 1/16; A61B 6/4241; A61B 6/5205; A61B 6/032

USPC .................. 702/106, 126, 189, 193; 250/214, 250/370.11; 378/19
See application file for complete search history.

(56) References Cited

U.S. PATENT DOCUMENTS 7,606,347 B2 * 10/2009 Tkaczyk et al. ................ 378/19
7,655,918 B2    2/2010 Liu et al.
(Continued)

FOREIGN PATENT DOCUMENTS

CN    101405620 A    4/2009
CN    101918858 A   12/2010
(Continued)

OTHER PUBLICATIONS

S.-M. Baek et al., "A Design of Single Pixel Photon Counter for Digital X-ray Image Sensor," *The Journal of the Korean Institute of Information and Communication Engineering*, vol. 11, No. 2, Feb. 2007, pp. 322-329 (in Korean, including English abstract).
(Continued)

*Primary Examiner* — John H Le
(74) *Attorney, Agent, or Firm* — NSIP Law

(57) ABSTRACT

An apparatus for distinguishing an energy band of a photon in a readout circuit that counts photons in multi-energy radiation incident onto a sensor for each energy band includes an integrator configured to accumulate an electric signal received from the sensor that has undergone photoelectric conversion from the photon; a comparator configured to compare an accumulated electric signal received from the integrator with one of a plurality of threshold values; and a signal processor configured to instruct sequential switching from one of the plurality of threshold values to another one of the plurality of threshold values according to a result of a comparison received from the comparator; and output a digital signal that distinguishes an energy band of the photon based on results received from the comparator of sequential comparisons of the accumulated electric signal with the plurality of threshold values.

17 Claims, 4 Drawing Sheets

(51) Int. Cl.
*A61B 6/03* (2006.01)
*A61B 6/00* (2006.01)
*G01T 1/16* (2006.01)
*G01T 1/29* (2006.01)

(56) References Cited

U.S. PATENT DOCUMENTS

2009/0140159 A1 6/2009 Tomita et al.
2011/0036988 A1 2/2011 Campbell et al.

FOREIGN PATENT DOCUMENTS

| CN | 201788281 U | 4/2011 |
|---|---|---|
| JP | 2006-29986 A | 2/2006 |
| JP | 2008-122167 A | 5/2008 |
| KR | 10-0960715 B1 | 5/2010 |

OTHER PUBLICATIONS

K.-Y. Sung et al., "A Design of Digital CMOS X-ray Image Sensor with 32×32 Pixel Array Using Photon Counting Type," *The Journal of the Korean Institute of Information and Communication Engineering*, vol. 12, No. 7, Jul. 2008, pp. 1235-1242 (in Korean, including English abstract).

Chinese Office Action issued on Nov. 5, 2015, in counterpart Chinese Application No. 201210284794.X (11 pages in English, 7 pages in Chinese).

\* cited by examiner

APPARATUS AND METHOD FOR DISTINGUISHING ENERGY BANDS OF PHOTONS IN MULTI-ENERGY RADIATION

CROSS-REFERENCE TO RELATED APPLICATIONS

This application claims the benefit of U.S. Provisional Application No. 61/522,782 filed on Aug. 12, 2011, and Korean Patent Application No. 10-2011-0101410 filed on Oct. 5, 2011, in the Korean Intellectual Property Office, the disclosures of which are incorporated herein by reference in their entirety.

BACKGROUND

1. Field

This disclosure relates to an apparatus and a method for distinguishing energy bands of photons in multi-energy radiation.

2. Description of the Related Art

Medical devices using radiation are currently available and continue to be developed. Along with the recent trend of analog to digital mode shifting in X-ray imaging systems using radiation, there have also been rapid advances in X-ray detectors as a core part of digital X-ray imaging systems. Digital X-ray detection technologies may be roughly classified into either indirect or direct methods. The indirect method generates an image via sequential conversions from X-rays to visible light and then from the visible light to an electric signal, and the direct method generates an image via direct conversion of an X-ray signal to an electric signal.

X-ray detection methods include an integration method in which an image signal is generated by integration of electric signals generated for a predetermined duration, and a photon counting method in which an image signal is generated by counting incident X-ray photons. The photon counting method creates a high quality image with distinguishable X-ray energy bands via a single exposure, i.e., a small exposure to X-rays, and accordingly vigorous research has recently been conducted thereon.

SUMMARY

According to an aspect, an apparatus for distinguishing energy band of photon in a readout circuit that counts photons in multi-energy radiation incident onto a sensor for each energy band includes an integrator configured to accumulate an electric signal received from the sensor that has undergone photoelectric conversion from the photon; a comparator configured to compare the accumulated electric signal received from the integrator with one of a plurality of threshold values; and a signal processor configured to instruct sequential switching from one of the plurality of threshold values to another one of the plurality of threshold values according to a result of a comparison received from the comparator; and output digital signal that distinguish the energy band of the photon based on results received from the comparator of sequential comparisons of the accumulated electric signal with the plurality of threshold values.

The signal corresponds to a result of a comparison of the accumulated electric signal with one of the plurality of threshold values.

The apparatus may further include a multiplexer configured to output one of the plurality of threshold values to the comparator in response to an instruction from the signal processor.

The signal processor may be further configured to, if the signal processor receives from the comparator a result of a comparison of the accumulated electric signal with a largest threshold value of the plurality of threshold values, instruct resetting of the integrator; and instruct the multiplexer to output a least threshold value of the plurality of threshold values.

The signal processor may be further configured to instruct the multiplexer to switch to a next threshold value of the plurality of threshold values if the signal processor receives from the comparator a result of a comparison indicating that the accumulated electric signal is higher than a current threshold value of the plurality of threshold values excluding a largest threshold value of the plurality of threshold values.

The signal processor may be further configured to instruct the multiplexer to switch to a next threshold value of the plurality of threshold values if the signal processor receives from the comparator a result of a comparison indicating that the accumulated electric signal is higher than a least threshold value of the plurality of threshold values.

The signal processor may be further configured to instruct the multiplexer to switch to a next threshold value of the plurality of threshold values if the signal processor receives from the comparator a result of a comparison indicating that the accumulated electric signal is higher than a current threshold value of the plurality of threshold excluding a largest threshold value of the plurality of threshold values.

The signal processor may be further configured to, if the signal processor receives from the comparator a result of a comparison indicating that the accumulated electric signal is lower than a current threshold value of the plurality of threshold values excluding the least threshold value, instruct resetting of the integrator; and instruct the multiplexer to output the least threshold value.

According to an aspect, a method of distinguishing energy band of photon in a readout circuit that counts photons in multi-energy radiation incident onto a sensor for each energy band includes accumulating an electric signal received from the sensor that has undergone photoelectric conversion from the photon; comparing the accumulated electric signal that is a result of the accumulating with one of a plurality of threshold values; instructing sequential switching from one of the plurality of threshold values to another one of the plurality of threshold values according to a result of the comparing; and outputting digital signal that distinguish the energy band of the photon based on results of sequential comparisons of the accumulated electric signal with the plurality of threshold values.

The digital signal corresponds to a result of comparing the accumulated electric signal with one of the plurality of threshold values.

The instructing may include instructing switching from a least threshold value of the plurality of threshold values to a next threshold value of the plurality of threshold values if a result of the comparing indicates that the accumulated electric signal is higher than the least threshold value.

The instructing further may include instructing switching from a current threshold value of the plurality of threshold values to a next threshold value of the plurality of threshold values if the result of the comparing indicates that the accumulated electric signal is higher than the current threshold value excluding a largest threshold value of the plurality of threshold values.

The instructing may include, if a result of the comparing indicates that the accumulated electric signal is lower than a current threshold value of the plurality of threshold values excluding a least threshold value of the plurality of threshold values, instructing resetting of the accumulated electric signal; and instructing switching from the current threshold value to the least threshold value.

The instructing may include, if a result of the comparing is a result of comparing the accumulated electric signal with a largest threshold value of the plurality of threshold values, instructing resetting of the accumulated electric signal; and instructing switching from the largest threshold value to a least threshold value of the plurality of threshold values.

The instructing may include instructing switching from a current threshold value of the plurality of threshold values to a next threshold value of the plurality of threshold values if a result of the comparing indicates that the accumulated electric signal is higher than the current threshold value excluding a largest threshold value of the plurality of threshold values.

According to an aspect, a non-transitory computer-readable storage medium stores a program for controlling a processor to perform the method described above.

An apparatus for distinguishing energy band of photon includes an integrator configured to receive an electric signal from a sensor that has photoelectrically converted photon into the electric signal; integrate the electrical signal to obtain an integrated electric signal; and output the integrated electric signal; a comparator configured to receive the integrated electric signal and a current threshold level of a plurality of threshold values; compare the integrated electric signal with the current threshold level; and output a result of the comparison; and a signal processor configured to receive the result of the comparison; instruct that the current threshold value be switched to another one of the threshold values based on the result of the comparison; and output a digital signal indicating which energy band of a plurality of energy bands of photons the accumulated electric signal is in based on the result of the comparison.

The signal processor may be further configured to output a control signal indicating which one of the plurality of threshold values the current threshold value is to be switched to; and the apparatus further may include a multiplexer configured to receive the plurality of threshold values; receive the control signal; and output the one of the plurality of threshold values indicated by the control signal as the current threshold value to the comparator.

The apparatus may further include a counter configured to receive the digital signal; and count the digital signal according to the energy band indicated by the digital signal.

The signal processor may be further configured to instruct that the current threshold value be switched to a next higher threshold value of the plurality of threshold values if a result of the comparison is that the integrated electric signal is higher than the current threshold value except when the current threshold value is a highest threshold value of the plurality of threshold values.

The signal processor may be further configured to instruct that the current threshold value be switched to a lowest threshold value of the plurality of threshold values if a result of the comparison is that the integrated electric signal is lower than the current threshold value except when the current threshold value is the lowest threshold value.

The signal processor may be further configured to output a reset signal indicating that the integrator is to be reset if a result of the comparison is that the integrated electric signal is lower than the current threshold value except when the current threshold value is the lowest threshold value; and the integrator may be further configured to receive the reset signal; and reset the integrated electric signal to zero in response to the reset signal.

Additional aspects will be set forth in part in the description that follows and, in part, will be apparent from the description, or may be learned by practice of the described examples.

BRIEF DESCRIPTION OF THE DRAWINGS

The above and other aspects will become apparent and more readily appreciated from the following description of examples, taken in conjunction with the accompanying drawings of which.

DETAILED DESCRIPTION

Figure 1:
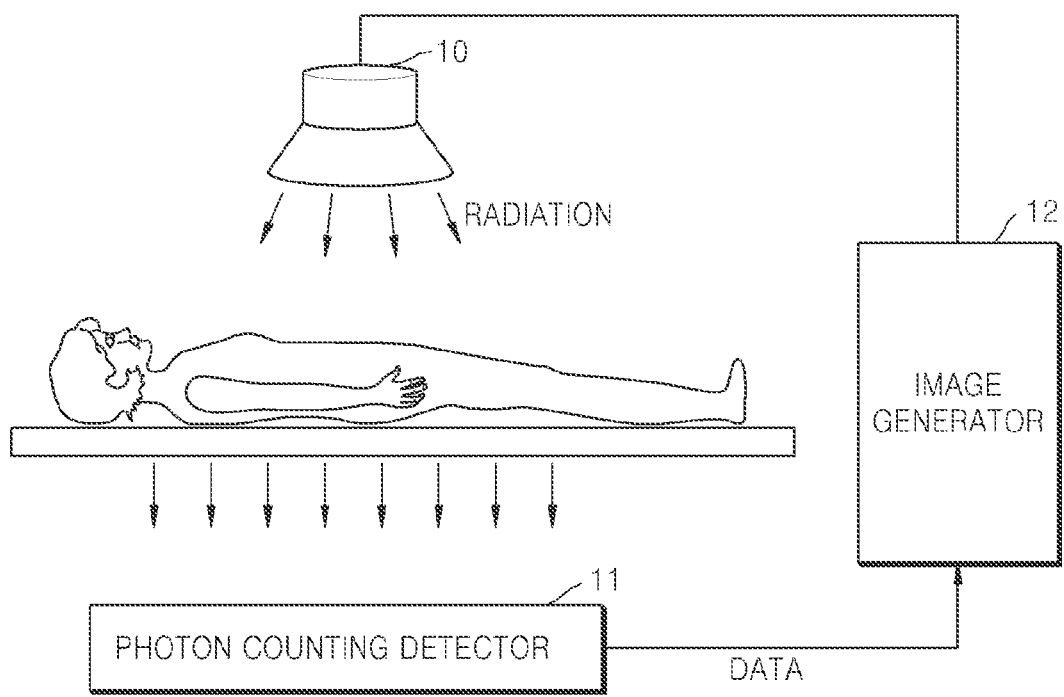
FIG. 1 is a diagram illustrating a configuration of a medical imaging system according to an example of this disclosure.

Reference will now be made in detail to examples that are illustrated in the accompanying drawings, wherein like reference numerals refer to like elements throughout. In this regard, the described examples may have different forms, and are not to be construed as being limited to the specific descriptions set forth herein. Accordingly, the examples are merely described below by referring to the figures to explain aspects of this disclosure.

FIG. 1 is a diagram illustrating a configuration of a medical imaging system according to an example of this disclosure. Referring to FIG. 1, the medical imaging system includes a radiation generator 10, a photon counting detector 11, and an image generator 12. The medical imaging system detects multi-energy radiation that has passed through an irradiation target like a body part by using a sensor, counts photons in the multi-energy radiation detected using the sensor with respect to each energy band, and generates an image of the body part for each energy band based on a result of the count. A degree of multi-energy radiation absorption of the irradiation target depends on the type and density of the target, and the energy band of the radiation. For example, bones absorb a large amount of X-rays, while muscles absorb less X-rays compared to bones. Thus, the radiation generated by the radiation generator 10 may include a different number of photons after being transmitted through a bone compared to after being transmitted through other body tissues. The number of photons for each energy band of the radiation generated by the radiation generator 10 after being transmitted through a target may differ between when the target is a bone and when the target is other body tissues. The image generator 12 generates a sharp X-ray image of body tissues based on the results of counting photons for each energy band by the photon counting detector 11.

The radiation generator 10 generates and radiates radiation onto a patient. The radiation generated by the radiation generator 10 may be, for example, any of ultrasonic waves, α-rays, β-rays, γ-rays, X-rays, and neutron rays. In general, radiation may refer to X-rays that may cause ionization, which is harmful to the human body. For convenience of explanation, the examples in this disclosure are described with emphasis on X-rays as an example. However, it will be understood by one of ordinary skill in the art that other radiation rays may be used to create an image for each energy band of the radiation based on data of photon counts for each energy band.

The photon counting detector 11 includes readout circuits that correspond to a shot region of the target to be imaged using radiation, and in particular, the readout circuits may correspond to pixels of the shot region, respectively. The photon counting detector 11 outputs the results of counts by the readout circuits to the image generator 12. The larger the number of pixels in the shot region, the larger the number of the readout circuits in the readout chip that respectively correspond to the pixels, and the higher the resolution of the images that the image generator 12 can generate. In other words, the smaller the pixel size, the higher the resolution of the images that can be generated.

One of the technical issues regarding the photon counting detector 11 is to implement small readout circuits for high-resolution image generation. Reducing the pixel size requires that the readout circuits be reduced in size to correspond to the pixels. The readout circuits disposed in an array form in the readout chip convert electric signals received from unit sensors that respectively correspond to the readout circuits with respect to each photon energy level into digital signals, and output the digital signals to the image generator 12. Each unit sensor, which occupies a partial region of the entire sensor, outputs an electric signal generated by the photons detected by a corresponding readout circuit of the readout chip through a unit output terminal of the unit sensor. The electric signal each readout circuit has received from the unit sensor may be read out in either a charge integration mode or a photon counting mode.

The charge integration mode uses a capacitor for integrating charges in which electric signals generated for a predetermined duration are integrated and are read out via an analog-to-digital converter (ADC). This mode integrates electric signals generated by photons in all energy bands, and thus fails to convert the electric signals into digital signals with respect to each photon energy band.

On the other hand, in the photon counting mode, a readout circuit compares an electric signal received from a unit sensor for detecting photon with a threshold value and outputs a digital signal indicating '1' or '0', and a counter counts occurrences of '2' and outputs data in digital form. The photon counting mode compares signal generated by single photon with a predetermined threshold value whenever each signal is generated, and counts the signal. The photon counting detector 11 may be implemented using readout circuits based on the photon counting mode, wherein the readout circuits count photons received from the corresponding unit sensors with respect to each photon energy band.

Figure 2:
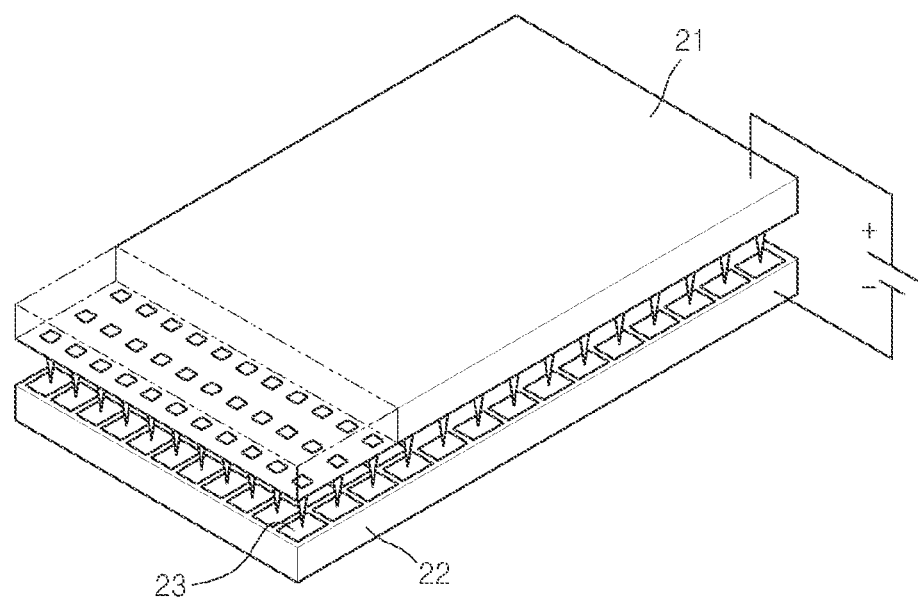
FIG. 2 is a perspective view of a photon counting detector of FIG. 1 according to an example of this disclosure.

FIG. 2 is a perspective view of the photon counting detector 11 of FIG. 1 according to an example of this disclosure. Referring to FIG. 2, the photon counting detector 11 includes a sensor 21 and a readout chip 22. The sensor 21 detects photons in the multi-energy radiation that has been transmitted through a target such as a body part, converts the detected photon into electric signal, and outputs the electric signal through unit output terminals of the sensor 12 to readout circuits 23 of the readout chip 22. The sensor 21 corresponds to a shot region, and a region of the sensor that corresponds to each pixel of the shot region is referred to as a 'unit sensor'. A unit sensor converts an incident photon into an electric signal and outputs the electric signal through a unit output terminal of the unit sensor.

The readout chip 22 corresponds in size to the shot region and the sensor 21, and includes the readout circuits 23 that respectively correspond to the pixels of the shot region. Thus, the size of the shot region determines the size of the readout chip 22. To form more pixels in a shot region having a particular size, the readout circuits 23 that are to respectively correspond to the pixels of the shot region need to be reduced in size. When the sizes of the readout circuits 12 are reduced so that the shot region of a particular size is divided into more pixels, a higher-resolution image with respect to each photon energy band may be generated in the shot region.

Figure 3:
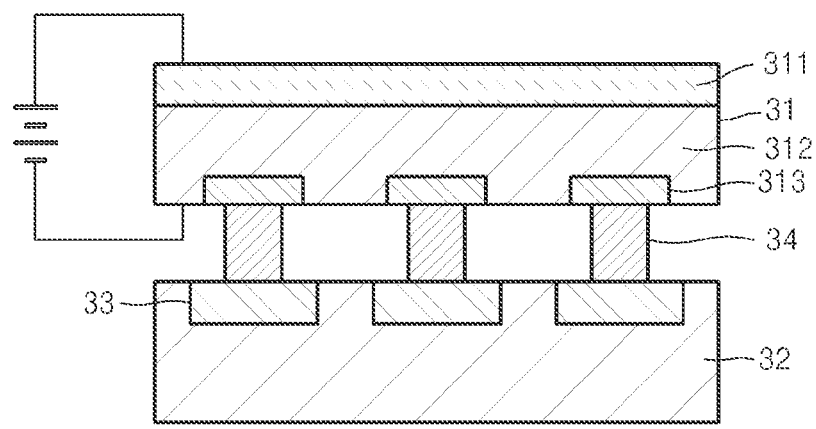
FIG. 3 is a cross-sectional view of a photon counting detector of FIG. 1 according to another example of this disclosure.

FIG. 3 is a cross-sectional view of the photon counting detector 11 of FIG. 1 according to another example of this disclosure. Referring to FIG. 3, the photon counting detector 11 includes a sensor 31 and a readout chip 32. The sensor 31 detects photons, converts them into electric signals, and outputs the converted electric signals to readout circuits 33 of the readout chip 32 that correspond to regions of the sensor 31 through bondings 34. When photons enter a depletion region 312 of the sensor 31, the sensor 31 generates electron-hole pairs, which are drawn by an electric field into a quasi-neutral n-region 311 and a quasi-neutral p-region 313 so that electric current flows out of the sensor 31. For example, when a multi-energy X-ray enters the sensor 31, the sensor 31 generates electric signals having different amplitudes with respect to energy bands of the photons in the multi-energy X-ray, and outputs the generated electric signals to the readout circuits 33 of the readout chip 32 through the quasi-neutral p-regions 313 that respectively correspond to unit sensors of the sensor 31. The quasi-neutral p-regions 313 are unit output terminals of unit sensors in the sensor 31. When photons are detected in the unit sensors of the sensor 31 that respectively correspond to the pixels of the shot region, the sensor 31 outputs electric signals through the unit output terminals of the unit sensors to the readout circuits 33 of the readout chip 32.

The sensor 31 generates the electric signals having different amplitudes with respect to the energy bands of the photons in the incident multi-energy X-ray according to the number of photons in the incident multi-energy X-ray. Upon receiving the photons, the sensor 31 may generate the electric signals, for example, with a time interval. The time interval in generating the electric signals may be sufficient for the photon counting detector 11 to distinguish the energy bands of the photons from the input electric signals. However, the time interval among the electric signals generated by the sensor 31 may be insufficient for the photon counting detector 11 to distinguish the energy bands of the photons, but this is less likely to occur. Thus, the time interval between the electric signals has merely a trivial effect on generation of the entire image.

Although in the embodiment of FIG. 3 the sensor 31 includes the quasi-neutral n-regions 311, the depletion region 312, and the quasi-neutral p-regions 313, it will be understood by one of ordinary skill in the art that any of a variety of sensors for detecting photons may be used. Also, although linked by bondings 34 in the embodiment of FIG. 3, the sensor 31 and the readout chip 32 may be connected by any of a variety of methods, for example, by vapor deposition.

The readout chip 32 is an array of the readout circuits 33 that respectively correspond to the unit sensors of the sensor 31. The readout circuits 33 distinguish the energy bands of the photons incident to the sensor 31 from the electric signals received from the sensor 31, which are generated by those photons in the sensor 31, count the photons in each energy band, and output the count data to the image generator 12. The readout chip 32 corresponds in size to the shot region, and the readout circuits 33 in the readout chip 32 respectively correspond to the pixels of the shot region. To generate high-resolution images, a shot region of a particular size needs to include a larger number of pixels, and thus the readout circuits 33 that respectively correspond to the pixels of the shot region need to be smaller in size. The image generator 12 generates an image with respect to each pixel of the shot region based on the result of counting photons in the readout circuit 33 that corresponds to the pixel.

The readout circuit 33 distinguishes the energy bands of photons in the incident multi-energy X-ray, outputs digital signals indicating the energy bands of the photons, and counts the photons in each energy band from the digital signals. Whenever an electric signal is received from a corresponding unit sensor, the readout circuit 33 compares an amplitude of the electric signal with predetermined threshold values to distinguish the energy levels of the photons in the multi-energy radiation, and counts the photons for each energy band. For example, as a result of comparing the electric signal received from the corresponding unit sensor with predetermined threshold values, if the amplitude of the electric signal received from the sensor 31 is found to be higher than a threshold value of 5V and lower than a threshold value of 6V, the readout circuit 33 generates a digital signal indicating the identified amplitude of the electric signal, and counts those digital signals for each energy band of the photons that have entered the sensor The bondings 34 connect the sensor 31 and the readout circuits 33 of the readout chip 32 to allow transfer of the electric signals generated in the regions of the sensor 31 to the corresponding readout circuits 33 of the readout chip 32. Although in the embodiment of FIG. 3 the sensor 31 and the readout circuits 33 of the readout chip 32 are linked by means of the bondings 34, any of a variety of methods may be used to connect the sensor 31 and the readout circuits 33 of the readout chip 32. For example, the sensor 31 may be connected to the readout chip 32 by using a semiconductor process, for example, using vapor deposition. However, it will be understood by one of ordinary skill in the art that any connecting method, not limited to bonding and evaporation, may be used.

Figure 4:
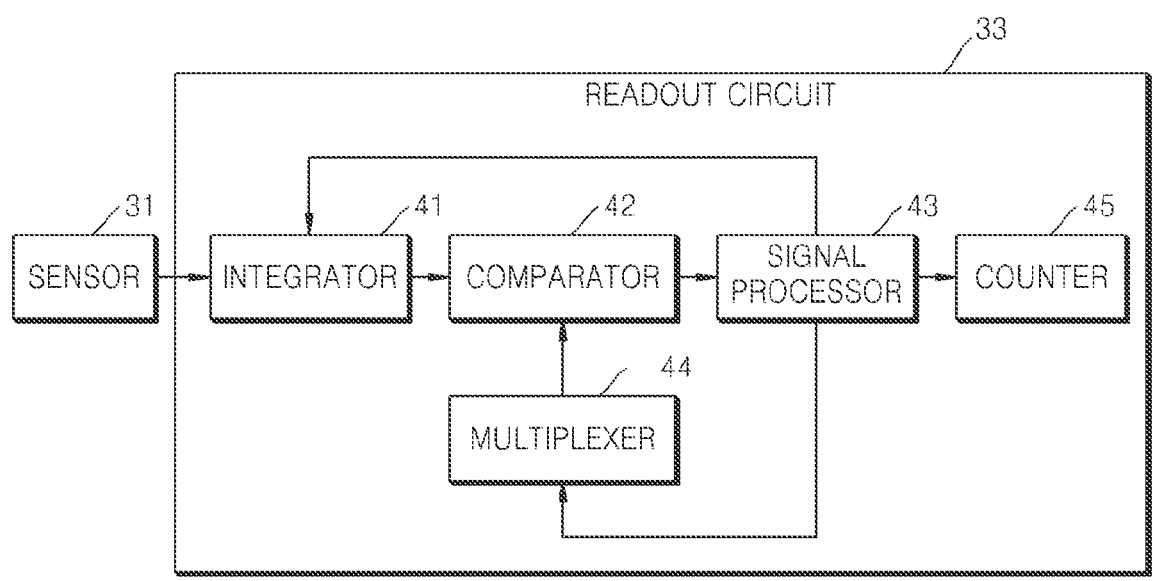
FIG. 4 is a block diagram of a readout circuit of FIG. 3 according to an example of this disclosure.

FIG. 4 is a block diagram of the readout circuit 33 of FIG. 3 according to an example of this disclosure. Referring to FIG. 4, the readout circuit 33 includes an integrator 41, a comparator 42, a signal processor 43, a multiplexer 44, and a counter 45. The integrator 41 accumulates an electric signal received from the sensor 31 that has been converted from a photon detected by the sensor 31, and outputs the accumulated signal to the comparator 42. The integrator 41 accumulates the electric signal input from the sensor 31 until a reset command is received from the signal processor 43, and returns to an initial state in which it was before the accumulation when the reset command is received from the signal processor 43. Until the reset command is received, the integrator 41 maintains a voltage level of the accumulated electric signal constant at an output terminal and continues to output the constant voltage level to the comparator 42. Thus, the integrator 41 outputs a non-pulsed signal, i.e., a signal that is invariant in amplitude, such as a DC voltage.

The comparator 42 compares the accumulated electric signal from the integrator 41 with a threshold value input from the multiplexer 44, and outputs a result of the comparison to the signal processor 43. The threshold value is a predetermined voltage level for dividing the entire energy band of photons in the multi-energy radiation into at least two energy bands. Thus, the use of more threshold values may allow a finer division into more photon energy bands for detecting the photons for each energy band.

The result of the comparison that the comparator 42 outputs to the signal processor 43 indicates whether the accumulated electric signal from the integrator 41 is higher in amplitude than a threshold value or vice versa. For example, the comparator 42 may output '1' if the accumulated electric signal from the integrator 41 is higher than a threshold value, and may output '0' if the accumulated electric signal from the integrator 41 is lower than the threshold value. Although in this example, the signal processor 43 outputs '2' if the accumulated electric signal is higher in amplitude than a threshold value and outputs '0' if not, the signal processor 43 may alternatively output '0' if the accumulated electric signal is higher in amplitude than a threshold value and output '1' if not.

The comparator 42 compares the accumulated electric signal from the integrator 41 with the threshold values input from the multiplexer 44 in sequence. In particular, the comparator 42 compares the accumulated electric signal from the integrator 41 with a threshold value input from the multiplexer 44, and outputs a result of the comparison to the signal processor 43. When the threshold value received from the multiplexer is changed, the comparator 42 compares the accumulated electric signal from the integrator 41 with that threshold value, and outputs a result of the comparison to the signal processor 43. The comparator 42 outputs a result of a comparison to the counter 45 whenever a threshold value received from the multiplexer is changed. Thus, the amplitude of the accumulated electric signal from the integrator 41 may be identified using only one comparator by performing a comparison with several threshold values in sequence.

Since the integrator 41 maintains a voltage level of the accumulated electric signal constant at the output terminal of the integrator 41, so that a constant accumulated electric signal is continuously output to the comparator 42, the comparator 42 is able to compare the accumulated electric signal input from the integrator 41 with the threshold values input from the multiplexer 44 in sequence at a relatively slow operation rate compared to if a pulsed signal were input to the comparator 42. If a pulsed signal is input from the integrator 41 to the comparator 42, the comparator 42 needs to operate at a higher rate to complete a comparison before the pulsed signal falls to a predetermined voltage level or less. However, in this example, while the integrator 41 maintains the voltage level of the accumulated electric signal constant until a reset command is received from the signal processor 43, the comparator 42 continues to receive the accumulated electric signal having the constant voltage level from the integrator 41 and compares the accumulated electric signal with the threshold values in sequence. In general, a relatively high-rate comparator needs a large amount of current relative compared to a low-rate comparator, and has a high power consumption. Since the accumulated electric signal having a constant voltage level is continuously input from the integrator 41 to the comparator 42, the comparator 42 does not need to operate at a high rate, and thus may operate with less current and a reduced power consumption.

The signal processor 43 receives the results of the sequential comparisons of the accumulated electric signal output from the integrator 41 with the threshold values from the comparator 42, and outputs a digital signal that indicates the energy band of the photon in the multi-energy radiation to the counter 45.

As a result of a comparison by the comparator 42, if the accumulated electric signal from the integrator 41 has a higher amplitude than a threshold value, the signal processor 43 instructs the multiplexer 44 to output a next threshold value to the comparator 42, and outputs a digital signal indicating that the amplitude of the accumulated electric signal is higher than the threshold value, to the counter 45. As a result of a comparison with the new threshold value, if the accumulated electric signal from the integrator 41 has a higher amplitude than the new threshold value, the above-described operations are repeated. The multiplexer 44 sequentially outputs the threshold values to the comparator 42 in ascending order, i.e., from the smallest threshold value to the largest threshold value.

On the other hand, as a result of the comparison with the new threshold value, if the accumulated electric signal from the integrator 41 has a lower amplitude than the new threshold value, the signal processor 43 outputs a digital signal indicating that the amplitude of the accumulated electric signal is lower than the new threshold value to the counter 45. If the accumulated electric signal from the integrator 41 has a lower amplitude than the new threshold value, the signal processor 43 outputs a reset command to the integrator 41 to reset the integrator 41, and instructs the multiplexer 44 to output the least threshold value to the comparator 42.

The signal processor 43 receives the results of the comparisons of the accumulated electric signal output from the integrator 41 with the threshold values from the comparator 42. The results of the comparisons input from the comparator 42 indicate which one of the accumulated electric signal from the integrator 41 and a threshold value is greater than the other. For example, the signal processor 43 may receive '1' from the comparator 42 if the accumulated electric signal from the integrator 41 is higher than a threshold value, and '0' from the comparator 42 if the accumulated electric signal from the integrator 41 is lower than a threshold value. Although in this example the signal processor 43 is described as receiving '1' from the comparator 42 if the accumulated electric signal is higher than a threshold value, the signal processor 43 may alternately receive '0' from the comparator 42 if the accumulated electric signal is higher than a threshold value.

The signal processor 43 outputs a corresponding digital signal to the counter 45 depending on which threshold value has been compared with the accumulated electric signal from the integrator 41 to obtain the result of the comparison received from the comparator 42. If the accumulated electric signal from the integrator 41 is lower than a threshold value that corresponds to an energy band of photons, the signal processor 43 outputs a digital signal indicating that the accumulated electric signal is lower than the corresponding threshold value to the counter 45. If the accumulated electric signal from the integrator 41 is higher than a threshold value that corresponds to an energy band of photons, the signal processor 43 outputs a digital signal indicating that the accumulated electric signal is higher than the corresponding threshold value to the counter 45. That is, the signal processor 43 is aware of which threshold value has been compared with the accumulated electric signal from the integrator 41 to obtain the result of the comparison received from the comparator 42 by control of the multiplexer 44, and outputs the results of the comparisons between the accumulated electric signal and the threshold values corresponding to the energy bands of photons as digital signals to the counter 45.

The signal processor 43 outputs a reset command to the integrator 41 to reset the integrator 41 to clear the electric signal accumulated by the integrator 41. That is, once an amplitude of the accumulated electric signal from the integrator 41 is identified through the comparison described above, the signal processor 43 instructs the integrator 41 to be reset to begin a new accumulation of electric signals input to the integrator 41.

For example, assuming that the accumulated electric signal from the integrator 41 is denoted by Vin, and the threshold values sequentially output from the multiplexer 44 are denoted by Vthd, Vth_low, Vth_mid, and Vth_high, Vthd indicates the least threshold value having an amplitude that corresponds to a leakage current or noise caused by the sensor 31, and Vth_low, Vth_mid, and Vth_high indicate threshold values that respectively correspond to the energy bands of photons. If the accumulated electric signal Vin is lower than the threshold value Vthd, it is unclear if the accumulated electric signal Vin is a leakage current or noise caused by the sensor 31, or an electric signal from photons, so the signal processor 43 does not instruct the integrator 41 to be reset to thereby allow the accumulation of electric signals input to the integrator 41 to continue, and does not instruct the multiplexer 44 to switch to a next threshold value.

If the accumulated electric signal Vin is higher than the threshold value Vthd, which means that the accumulated electric signal Vin is an electric signal from photons, the signal processor 43 does not instruct the integrator 41 to be reset, but instructs the multiplexer 44 to switch to the threshold value Vth_low from the threshold value Vthd so that the comparator 42 compares the accumulated electric signal Vin with the threshold value Vth_low.

If the accumulated electric signal Vin is less than the threshold value Vth_low, the signal processor 43 instructs the integrator 41 to be reset and instructs the multiplexer 44 to switch to the threshold value Vthd so that the comparator 42 compares an accumulated electric signal Vin obtained after the reset of the integrator 41 with the threshold value Vthd. The signal processor 43 outputs a digital signal indicating that the accumulated electric signal Vin is lower than the threshold value Vth_low to the counter 45.

If the accumulated electric signal Vin is higher than the threshold value Vth_low, which means that the accumulated electric signal Vin is an electric signal from photons, the signal processor 43 does not instruct the integrator 41 to be reset, and instructs the multiplexer 44 to switch the threshold value Vth_low to the threshold value Vth_mid so that the comparator 42 compares the accumulated electric signal Vin with the threshold value Vth_mid. The signal processor 43 outputs a digital signal indicating that the accumulated electric signal Vin is higher than the threshold value Vth_low to the counter 45.

If the accumulated electric signal Vin is lower than the threshold value Vth_mid, the signal processor 43 instructs the integrator 43 to be reset and instructs the multiplexer 44 to switch the threshold value Vth_mid to the threshold value Vthd. The signal processor 43 outputs a digital signal indicating that the accumulated electric signal Vin is lower than the threshold value Vth_mid to the counter 45.

If the accumulated electric signal Vin is higher than the threshold value Vth_mid, the signal processor 43 does not instruct the integrator 41 to be reset, and instructs the multiplexer 44 to switch the threshold value Vth_mid to the threshold value Vth_high so that the comparator 42 compares the accumulated electric signal Vin with the threshold value Vth_high. The signal processor 43 outputs a digital signal indicating that the accumulated electric signal Vin is higher than the threshold value Vth_mid to the counter 45.

If the accumulated electric signal Vin is lower than the threshold value Vth_high, the signal processor 43 instructs the integrator 41 to be reset and instructs the multiplexer 44 to switch the threshold value Vth_high to the threshold value Vthd. The signal processor 43 outputs a digital signal indicating that the accumulated electric signal Vin is lower than the threshold value Vth_high to the counter 45.

If the accumulated electric signal Vin is higher than the threshold value Vth_high, the signal processor 43 instructs the integrator 41 to be reset and instructs the multiplexer 44 to switch the threshold value Vth_high to the threshold value Vthd. The signal processor 43 outputs a digital signal indicating that the accumulated electric signal Vin is higher than the threshold value Vth_high to the counter 45.

The threshold values Vthd, Vth_low, Vth_mid, and Vth_high may be from the least to the greatest in this order, that is, Vthd<Vth_low<Vth_mid<Vth_high. Vthd is the least value of these threshold values.

Although the above example describes the use of four threshold values including the least threshold value Vthd, an arbitrary number N of threshold values excluding the least threshold value Vthd may be used, and the least threshold value Vthd and the N threshold values may be sequentially compared with the accumulated electric signal Vin. As a result, if the accumulated electric signal Vin is smaller than all of the N threshold values, i.e., if the accumulated electric signal Vin is smaller than all of those threshold values that are indicative of the different energy bands of photons, i.e., the N threshold values, the signal processor 43 may instruct the integrator 41 to be reset.

The threshold value Vthd is a threshold value indicative of whether the accumulated electric signal Vin from the integrator 41 is a leakage current or noise caused by the sensor 31. The amplitude of a leakage current caused by the sensor 31 may be obtained by measuring an amplitude of a current generated by the sensor 31 alone in a non-radiation condition. The threshold value Vthd may be a voltage level previously set according to the measured amplitude of the leakage current, and may be compared with the accumulated electric signal Vin from the integrator 41 to determine whether the accumulated electric signal Vin from the integrator 41 is from a leakage current caused by the sensor 31, rather than from photons in the radiation.

The threshold values Vth_low, Vth_mid, and Vth_high are voltage levels that are previously set for distinguishing several energy bands of the photons, and may be set based on measurements of the amplitudes of electric signals the sensor 31 generates according to the different energy bands of the photons, so that the energy bands of the photons detected by the sensor 31 may be divided.

Digital signals that the signal processor 43 outputs to the counter 45 based on the results of the comparisons from the comparator 42 are as follows. OUT_low="0" is a digital signal indicating that the accumulated electric signal from the integrator 41 is less than the threshold value Vth_low, and OUT_low="1" is a digital signal indicating that the accumulated electric signal from the integrator 41 is higher than the threshold value Vth_low. OUT_mid="0" is a digital signal indicating that the accumulated electric signal from the integrator 41 is less than the threshold value Vth_mid, and OUT_mid="1" is a digital signal indicating that the accumulated electric signal from the integrator 41 is higher than the threshold value Vth_mid. OUT_high="0" is a digital signal indicating that the accumulated electric signal from the integrator 41 is less than the threshold value Vth_high, and OUT_high="1" is a digital signal indicating that the accumulated electric signal from the integrator 41 is higher than the threshold value Vth_high. Although in the above examples "1" and "0" are described as indicating high and low levels, respectively, "0" and "1" may indicate high and low levels, respectively. It will be understood by one of ordinary skill in the art that signals for outputting the results of the comparisons may be in any of a variety of forms.

The multiplexer 44 sequentially outputs the threshold values that are sequentially switched from one to another according to a command from the signal processor 43 to the comparator 42. The multiplexer 44 outputs the threshold value Vthd to the comparator 42. If the accumulated electric signal from the integrator 41 is higher than the threshold value Vthd, the multiplexer 44 outputs a next threshold value Vth_low to the comparator 42 according to a command from the signal processor 43. If the accumulated electric signal from the integrator 41 is higher than the threshold value Vth_low, the multiplexer 44 outputs a next threshold value Vth_mid to the comparator 42 according to a command from the signal processor 43. These processes are repeated if the accumulated electric signal from the integrator 41 is higher than a threshold output from the multiplexer 44 until the multiplexer 44 outputs the threshold value Vth_high. The threshold values Vthd, Vth_low, Vth_mid, and Vth_high may be from the least to the greatest in this order.

The counter 45 counts photons with respect to each energy band according to the digital signals received from the signal processor 43. The counter 45 receives digital signals indicative of the different amplitudes of the accumulated electric signals from the integrator 41. For example, as discussed above, the digital signals received from the signal processor 43 may include OUT_low="0", OUT_low="1", OUT_mid="0", OUT_mid="1", OUT_high="0", and OUT_high="1".

The counter 45 may include three counters Low_counter, Mid_counter, and High_counter (not shown). The counter Low_counter counts photons having an energy band that corresponds to the threshold value Vth_low, the counter Mid_counter counts photons having an energy band that corresponds to the threshold value Vth_mid, and the counter High_counter counts photons having an energy band that corresponds to the threshold value Vth_high.

When the counter 45 receives OUT_low="1" from the signal processor 43, the counter Low_counter counts the digital signal. When the counter 45 receives OUT_mid="1" from the signal processor 43, the counter Mid_counter counts the digital signal. When the counter 45 receives OUT_high="1" from the signal processor 43, the counter High_counter counts the digital signal. As described above, the three counters Low_counter, Mid_counter and High_counter of the counter 45 receive and count the digital signals indicating the different photon energy bands with respect to each photon energy band from the signal processor 43.

These counters Low_counter, Mid_counter and High_counter may be digital counters. Digital counters, which are circuits for counting constant clock inputs in a predetermined order, may be classified into either up-counters or down-counters depending on the direction in which clock inputs are counted. For example, if the counters Low_counter, Mid_counter, and High_counter are up-counters, the counters Low_counter, Mid_counter and High_counter increase the count of photons by one whenever receiving a corresponding digital signal from the signal processor 43, and store the same. For example, if the counter 45 receives OUT_low="1" from the signal processor 43 three times, the counter Low_counter counts the digital signal three times, and stores number "3".

Figure 5:
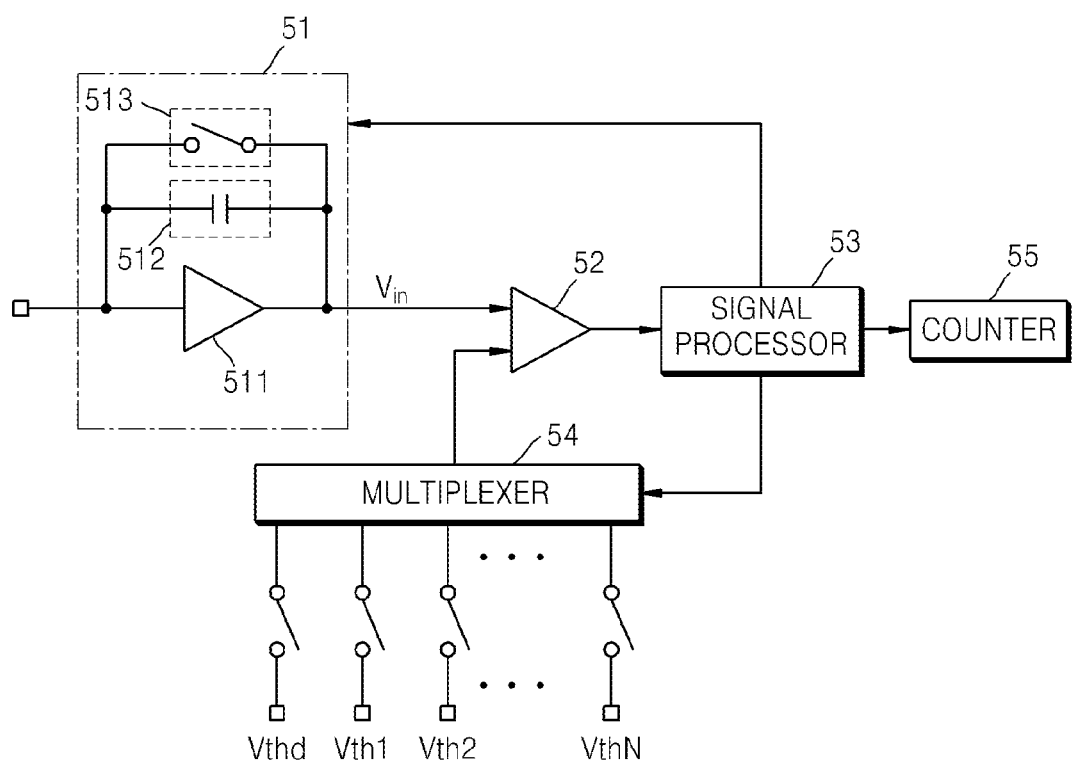
FIG. 5 is a circuit diagram of a readout circuit of FIG. 3 according to an example of this disclosure.

FIG. 5 is a circuit diagram of the readout circuit 33 of FIG. 3 according to an example of this disclosure, in which only some elements of the readout circuit 33 of FIG. 4 are illustrated in detail. Therefore, although not explicitly described in this example, any content described above in connection with the readout circuit 33 shall apply to the readout circuit of FIG. 5 according to this example. Referring to FIG. 5, the readout circuit 33 includes an integrator 51, a comparator 52, a signal processor 53, a multiplexer 54, and a counter 45.

The integrator 51 includes an amplifier 511, a capacitor 512, and a switch 513. The amplifier 511 is connected in parallel with the capacitor 512 and the switch 513. That is, the capacitor 512 and the switch 513 are connected to both input and output terminals of the amplifier 511. When the amplifier 511 and the capacitor 512 are connected in parallel, a current input to the integrator 51 fails to flow into the amplifier 512 because of a high resistance at the input terminal of the amplifier 511, and thus is accumulated in the capacitor 512. The charges accumulated in the capacitor 512 produce a voltage difference between the opposite terminals of the capacitor 512, causing a voltage level Vin at the output terminal of the amplifier 511 to be higher than a voltage level at the input terminal of the amplifier 511 by the voltage difference between the opposite terminals of the capacitor 512. The voltage Vin at the output terminal of the amplifier 511 is an accumulated electric signal that is input to the comparator 52. A voltage V(t) between the opposite terminals of the capacitor 512 may be calculated using the following Equation 1:

$$V(t) = \frac{1}{C} \int_0^t I(\tau) d\tau + V(0) \quad (1)$$

where C is an capacitance of the capacitor 512, I(τ) is a current input to the integrator 51, and V(0) is an initial voltage of the capacitor 512. t is time of integration, and τ is variable of integration.

The switch 513 is responsive to a reset command that is output from the signal processor 53. When the integrator 51 receives the reset command from the signal processor 53, the switch 513 closes, thereby discharging the charges accumulated in the capacitor 512 and resetting the accumulated electric signal Vin to zero, thereby resetting the integrator 51 to an initial state in which it was before the charges began being accumulated in the capacitor 512.

The multiplexer 54, which includes as many switches as there are threshold values, sequentially outputs the threshold values to the comparator 52 by controlling the operations of the switches. The switches are respectively connected to external voltage sources. The voltage sources provide voltages having amplitudes corresponding to the threshold values Vthd, Vth_low, Vth_mid, and Vth_high. The multiplexer 54 switches on one of the switches according to a command from the signal processor 53 to output a voltage from the voltage source connected to that switch. For example, with the assumption that a first switch of the multiplexer 54 is connected to a voltage source that provides a voltage corresponding to the threshold value Vthd, if the first switch is switched on, the multiplexer 54 outputs the threshold value Vthd to the comparator 52.

Figure 6:
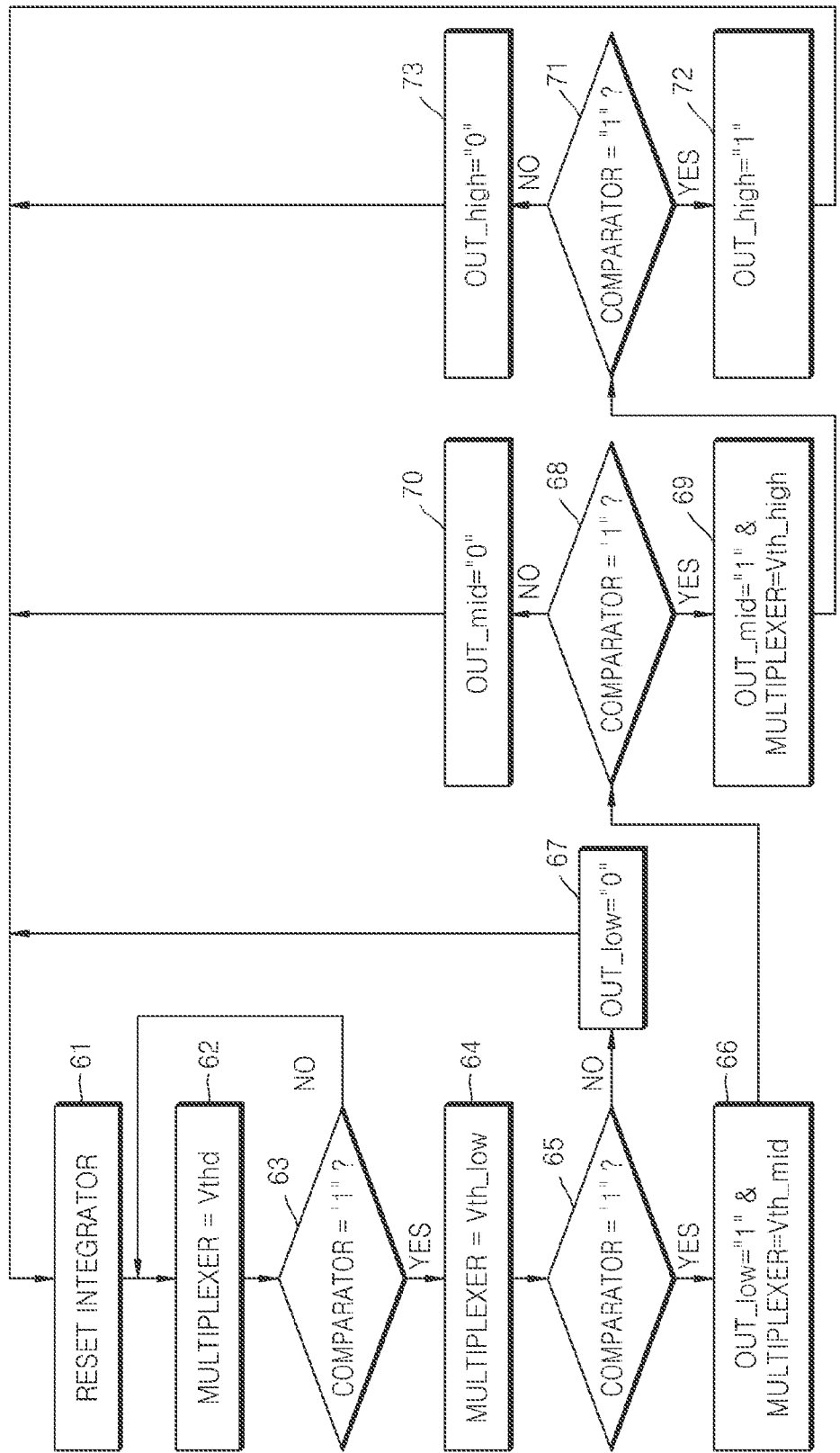
FIG. 6 is a flowchart of a method of distinguishing several energy bands of photons according to an example of this disclosure.

FIG. 6 is a flowchart of a method of distinguishing several energy bands of photons according to an example of this disclosure. Referring to FIG. 6, the method of distinguishing several energy bands of photons includes processes that are performed in time series in the readout circuit 33 of FIG. 4. Although not explicitly described below, any content described above in connection with the readout circuit 33 shall apply to the method of distinguishing several energy bands of photons according to the current embodiment. A photon counting method using one comparator in the readout circuit 33 may include the following operations.

In operation 61, the signal processor 43 instructs the integrator 41 to be reset. In response to a reset command from the signal processor 43, the integrator 41 is reset to an initial state in which no signal is accumulated.

In operation 62, the signal processor 43 instructs the multiplexer 44 to output the threshold value Vthd to the comparator 42.

In operation 63, the signal processor 43 performs operation 64 if the result of a comparison received from the comparator 42 is "1", and performs operation 62 if the result of a comparison received from the comparator 42 is "0". If the result of a comparison the signal processor 43 has received from the comparator 42 is "1", this means that the accumulated electric signal from the integrator 41 is higher than the threshold value Vthd. If the result of a comparison the signal processor 43 has received from the comparator 42 is "0", this means that the accumulated electric signal from the integrator 41 is less than the threshold value Vthd.

In operation 64, the signal processor 43 instructs the multiplexer 44 to switch to the threshold value Vth_low from the threshold value Vthd. The multiplexer 44 may switch from one threshold value to another threshold value that is to be output to the comparator 42 according to a command from the signal processor 43.

In operation 65, the signal processor 43 performs operation 66 if the result of a comparison received from the comparator 42 is "1", and performs operation 67 if the result of a comparison received from the comparator 42 is "0". If the result of a comparison the signal processor 43 has received from the comparator 42 is "1", this means that the accumulated electric signal from the integrator 41 is higher than the threshold value Vth_low. If the result of a comparison the signal processor 43 has received from the comparator 42 is "0", this means that the accumulated electric signal from the integrator 41 is less than the threshold value Vth_low.

In operation 66, the signal processor 43 outputs a digital signal OUT_low="1" to the counter 45, and instructs the multiplexer 44 to switch to a next threshold value Vth_mid. The signal processor 43 outputs the digital signal OUT_low="1" to the counter 45 to enable counting by the counter Low_counter in the counter 45. The signal processor 43 instructs the multiplexer 44 to switch to and output a next threshold value Vth_mid to the comparator 42. In operation 68, the comparator 42 compares the accumulated electric signal from the integrator 41 with the threshold value Vth_mid.

In operation 67, the signal processor 43 outputs a digital signal OUT_low="0" to the counter 45, and returns to operation 61. When the signal processor 43 outputs the digital signal OUT_low="0" to the counter 45, the counter 45 does not perform counting.

In operation 68, the signal processor 43 performs operation 69 if the result of a comparison received from the comparator 42 is "1", and performs operation 70 if the result of a comparison received from the comparator 42 is "0". If the result of a comparison the signal processor 43 has received from the comparator 42 is "1", this means that the accumulated electric signal from the integrator 41 is higher than the threshold value Vth_mid. If the result of a comparison the signal processor 43 has received from the comparator 42 is "0", this means that the accumulated electric signal from the integrator 41 is less than the threshold value Vth_mid.

In operation 69, the signal processor 43 outputs a digital signal OUT_mid="1" to the counter 45, and instructs the multiplexer 44 to switch to a next threshold value Vth_high. The signal processor 43 outputs the digital signal OUT_mid="1" to the counter 45 to enable counting by the counter Mid_counter in the counter 45. The signal processor 43 instructs the multiplexer 44 to switch to and output a next threshold value Vth_high to the comparator 42. In operation 71, the comparator 42 compares the accumulated electric signal from the integrator 41 with the threshold value Vth_high.

In operation 70, the signal processor 43 outputs a digital signal OUT_mid="0" to the counter 45, and returns to operation 61. When the signal processor 43 outputs the digital signal OUT_mid="0" to the counter 45, the counter 45 does not perform counting.

In operation 71, the signal processor 43 performs operation 72 if the result of a comparison received from the comparator 42 is "1", and performs operation 73 if the result of a comparison received from the comparator 42 is "0". If the result of a comparison the signal processor 43 has received from the comparator 42 is "1", this means that the accumulated electric signal from the integrator 41 is higher than the threshold value Vth_high. If the result of a comparison the signal processor 43 has received from the comparator 42 is "0", this means that the accumulated electric signal from the integrator 41 is less than the threshold value Vth_high.

In operation 72, the signal processor 43 outputs a digital signal OUT_high="1" to the counter 45, and returns to operation 61. The signal processor 43 outputs the digital signal OUT_high="1" to the counter 45 to enable counting by the counter High_counter in the counter 45.

In operation 73, the signal processor 43 outputs a digital signal OUT_high="0" to the counter 45, and returns to operation 61. When the signal processor 43 outputs the digital signal OUT_high="0" to the counter 45, the counter 45 does not perform counting.

The signal processor 43 controls the above described processes to enable sequential comparisons of the accumulated electric signal from the integrator 41 with several threshold values so that the results of the comparisons are output to the counter 45.

As described above, according to the various examples of this disclosure, photons in multi-energy radiation may be divided according to energy bands using only one comparator, leading to a reduction in size of a photon energy band dividing apparatus. A leakage current and noise caused by a sensor are removed based on the result of a comparison with the least threshold value.

The various elements in FIGS. 4 and 5 may be implemented using hardware components and/or software components. Software components may be implemented by a processing device, which may be implemented using one or more general-purpose or special-purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purposes of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

As used herein, a processing device configured to implement a function A includes a processor programmed to run specific software. In addition, a processing device configured to implement a function A, a function B, and a function C may include configurations, such as, for example, a processor configured to implement functions A, B, and C; a first processor configured to implement function A and a second processor configured to implement functions B and C; a first processor configured to implement functions A and B and a second processor configured to implement function C; a first processor to implement function A, a second processor configured to implement function B, and a third processor configured to implement function C; a first processor configured to implement functions A, B, C and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion.

In particular, the software and data may be stored by one or more non-transitory computer-readable storage mediums. The non-transitory computer-readable storage medium may include any data storage device that can store data that can be thereafter read by a computer system or processing device. Examples of a non-transitory computer-readable storage medium include read-only memory (ROM), random-access memory (RAM), CD-ROMs, magnetic tapes, floppy disks, and optical data storage devices. Also, functional programs, codes, and code segments for implementing the examples disclosed herein can be easily constructed by programmers skilled in the art to which the examples pertain based on the drawings and their corresponding descriptions as provided herein.

While this disclosure has been particularly shown and described with reference to examples thereof, it will be understood by those skilled in the art that various changes in form and details may be made in these examples without departing from the spirit and scope of the invention as defined by the claims and their equivalents. The examples are to be considered in a descriptive sense only, and not for purposes of limitation. Descriptions of features or aspects in one example are to be considered as being applicable to similar features or aspects in other examples. Suitable results may be achieved if the described techniques are performed in a different order and/or if components in a described system, architecture, device, or circuit are combined in a different manner and/or replaced or supplemented by other components or their equivalents. Therefore, the scope of the invention is defined not by the detailed description of the disclosure, but by the claims and their equivalents, and all variations within the scope of the claims and their equivalents are to be construed as being included in the invention.

What is claimed is:

1. An apparatus for distinguishing an energy band of a photon in a readout circuit that counts photons in multi-energy radiation incident onto a sensor for each energy band, the apparatus comprising:
   an integrator configured to accumulate an electric signal received from the sensor that has undergone photoelectric conversion from the photon;
   a comparator configured to compare an accumulated electric signal received from the integrator with one of a plurality of threshold values; and a signal processor configured to:
  instruct sequential switching from one of the plurality of threshold values to another one of the plurality of threshold values according to a result of a comparison received from the comparator; and
  output a digital signal that distinguishes an energy band of the photon based on results received from the comparator of sequential comparisons of the accumulated electric signal with the plurality of threshold values,
  wherein each of the plurality of threshold values is a predetermined voltage level that distinguishes an energy band from among a plurality of energy bands of photons in the multi-energy radiation.

2. The apparatus of claim 1, wherein the digital signal corresponds to a result of a comparison of the accumulated electric signal with one of the plurality of threshold values.

3. The apparatus of claim 1, further comprising a multiplexer configured to output one of the plurality of threshold values to the comparator in response to an instruction from the signal processor.

4. The apparatus of claim 3, wherein the signal processor is further configured to, if the signal processor receives from the comparator a result of a comparison of the accumulated electric signal with a largest threshold value of the plurality of threshold values:
  instruct resetting of the integrator; and
  instruct the multiplexer to output a least threshold value of the plurality of threshold values.

5. The apparatus of claim 3, wherein the signal processor is further configured to instruct the multiplexer to switch to a next threshold value of the plurality of threshold values if the signal processor receives from the comparator a result of a comparison indicating that the accumulated electric signal is higher than a current threshold value of the plurality of threshold values excluding a largest threshold value of the plurality of threshold values.

6. The apparatus of claim 3, wherein the signal processor is further configured to instruct the multiplexer to switch to a next threshold value of the plurality of threshold values if the signal processor receives from the comparator a result of a comparison indicating that the accumulated electric signal is higher than a least threshold value of the plurality of threshold values.

7. The apparatus of claim 6, wherein the signal processor is further configured to instruct the multiplexer to switch to a next threshold value of the plurality of threshold values if the signal processor receives from the comparator a result of a comparison indicating that the accumulated electric signal is higher than a current threshold value of the plurality of threshold excluding a largest threshold value of the plurality of threshold values.

8. The apparatus of claim 6, wherein the signal processor is further configured to, if the signal processor receives from the comparator a result of a comparison indicating that the accumulated electric signal is lower than a current threshold value of the plurality of threshold values excluding the least threshold value:
  instruct resetting of the integrator; and
  instruct the multiplexer to output the least threshold value.

9. A method of distinguishing an energy band of a photon in a readout circuit that counts photons in multi-energy radiation incident onto a sensor for each energy band, the method comprising:
  accumulating, by an integrator, an electric signal received from the sensor that has undergone photoelectric conversion from the photon;
  comparing, by a comparator, an accumulated electric signal that is a result of the accumulating with one of a plurality of threshold values;
  instructing, by a signal processor, sequential switching from one of the plurality of threshold values to another one of the plurality of threshold values according to a result of the comparing; and
  outputting, by the signal processor, a digital signal that distinguishes the energy band of the photon based on results of sequential comparisons of the accumulated electric signal with the plurality of threshold values,
  wherein each of the plurality of threshold values is a predetermined voltage level that distinguishes an energy band from among a plurality of energy bands of photons in the multi-energy radiation.

10. The method of claim 9, wherein the digital signal corresponds to a result of comparing the accumulated electric signal with one of the plurality of threshold values.

11. The method of claim 9, wherein the instructing comprises instructing switching from a least threshold value of the plurality of threshold values to a next threshold value of the plurality of threshold values if a result of the comparing indicates that the accumulated electric signal is higher than the least threshold value.

12. The method of claim 11, wherein the instructing further comprises instructing switching from a current threshold value of the plurality of threshold values to a next threshold value of the plurality of threshold values if the result of the comparing indicates that the accumulated electric signal is higher than the current threshold value excluding a largest threshold value of the plurality of threshold values.

13. The method of claim 9, wherein the instructing comprises, if a result of the comparing indicates that the accumulated electric signal is lower than a current threshold value of the plurality of threshold values excluding a least threshold value of the plurality of threshold values:
  instructing resetting of the accumulated electric signal; and
  instructing switching from the current threshold value to the least threshold value.

14. The method of claim 9, wherein the instructing comprises, if a result of the comparing is a result of comparing the accumulated electric signal with a largest threshold value of the plurality of threshold values:
  instructing resetting of the accumulated electric signal; and
  instructing switching from the largest threshold value to a least threshold value of the plurality of threshold values.

15. The method of claim 9, wherein the instructing comprises instructing switching from a current threshold value of the plurality of threshold values to a next threshold value of the plurality of threshold values if a result of the comparing indicates that the accumulated electric signal is higher than the current threshold value excluding a largest threshold value of the plurality of threshold values.

16. A method of distinguishing energy bands of photons in a readout circuit that counts photons in multi-energy radiation incident onto a sensor for each energy band, the method comprising:
  receiving, by a signal processor, a result of a comparison of an accumulated electric signal that is cumulatively received from the sensor after being converted from a photon with one of a plurality of threshold values;
  instructing, by the signal processor, sequential switching from one of the plurality of threshold values to another one of the plurality of threshold values according to the result of the comparison; and outputting, by the signal processor, a digital signal that distinguishes an energy band of the photon based on results of sequential comparisons with the plurality of threshold values, wherein each of the plurality of threshold values is a predetermined voltage level that distinguishes an energy band from among a plurality of energy bands of photons in the multi-energy radiation.

17. A non-transitory computer-readable storage medium storing a program for controlling a processor to perform the method of claim 16.

* * * * *